United States Patent
Janke et al.

[11] Patent Number: 6,097,986
[45] Date of Patent: *Aug. 1, 2000

[54] RETRACTABLE LEAD WITH MESH SCREEN

[75] Inventors: Aaron W. Janke; Mary Lee Cole, both of St. Paul, Minn.

[73] Assignee: Cardiac Pacemakers, Inc., St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/992,039

[22] Filed: Dec. 17, 1997

[51] Int. Cl.⁷ ............................................. A61N 1/05
[52] U.S. Cl. .......................... 607/127; 607/126; 600/375
[58] Field of Search .................................. 607/116, 122, 607/119, 126, 127, 130, 131; 600/372, 373, 374, 375

[56] References Cited

U.S. PATENT DOCUMENTS

| | | | |
|---|---|---|---|
| 4,106,512 | 8/1978 | Bisping | 128/418 |
| 4,217,913 | 8/1980 | Dutcher | 128/785 |
| 4,235,246 | 11/1980 | Weiss | 128/758 |
| 4,299,239 | 11/1981 | Weiss et al. | 128/785 |
| 4,311,153 | 1/1982 | Smits | 128/785 |
| 4,463,765 | 8/1984 | Gold | 128/785 |
| 4,570,642 | 2/1986 | Kane et al. | 128/785 |
| 4,624,265 | 11/1986 | Grassi | 128/784 |
| 4,624,266 | 11/1986 | Kane | 128/785 |
| 4,646,755 | 3/1987 | Kane | 128/785 |
| 4,649,938 | 3/1987 | McArthur | 128/785 |
| 4,664,113 | 5/1987 | Frisbie et al. | 128/344 |
| 4,819,661 | 4/1989 | Heil, Jr. et al. | 607/127 |
| 4,886,074 | 12/1989 | Bisping | 128/785 |
| 4,924,881 | 5/1990 | Brewer | 128/785 |
| 4,967,766 | 11/1990 | Bradshaw | 128/785 |
| 5,056,516 | 10/1991 | Spehr | 128/419 |
| 5,076,285 | 12/1991 | Hess et al. | 128/186 |
| 5,129,404 | 7/1992 | Spehr et al. | 128/785 |
| 5,143,090 | 9/1992 | Dutcher et al. | 607/121 |
| 5,152,299 | 10/1992 | Soukup | 128/785 |
| 5,181,526 | 1/1993 | Yamaski | 607/211 |
| 5,217,028 | 6/1993 | Dutcher et al. | 128/785 |
| 5,259,394 | 11/1993 | Bens | 607/127 |
| 5,259,395 | 11/1993 | Li | 607/131 |
| 5,282,845 | 2/1994 | Bush et al. | 607/128 |
| 5,300,108 | 4/1994 | Rebell et al. | 607/127 |
| 5,342,414 | 8/1994 | Mehra | 607/127 |
| 5,344,439 | 9/1994 | Otten | 607/126 |
| 5,358,516 | 10/1994 | Myers et al. | 607/116 |
| 5,374,286 | 12/1994 | Morris | 607/119 |
| 5,425,755 | 6/1995 | Doan | 607/119 |
| 5,425,756 | 6/1995 | Heil, Jr. et al. | 607/128 |
| 5,447,533 | 9/1995 | Vachon et al. | 607/120 |
| 5,447,534 | 9/1995 | Jammet | 607/127 |
| 5,456,708 | 10/1995 | Doan et al. | 607/127 |
| 5,476,501 | 12/1995 | Stewart et al. | 607/127 |
| 5,492,119 | 2/1996 | Abrams | 128/642 |
| 5,522,119 | 6/1996 | Gates | 607/127 |
| 5,531,780 | 7/1996 | Vachon | 607/120 |
| 5,728,140 | 3/1998 | Salo et al. | 607/9 |
| 5,871,529 | 2/1999 | Bartig et al. | 607/122 |

FOREIGN PATENT DOCUMENTS

| | | | |
|---|---|---|---|
| 0282047 | 9/1988 | European Pat. Off. | 607/127 |
| 0337035 | 10/1989 | European Pat. Off. | 607/127 |
| 0452278 | 10/1991 | European Pat. Off. | A61N 1/05 |
| 0672431 | 9/1995 | European Pat. Off. | A61N 1/05 |
| 2949782 | 6/1981 | Germany | 607/127 |

*Primary Examiner*—Kennedy J. Schaetzle
*Attorney, Agent, or Firm*—Schwegman, Lundberg, Woessner & Kluth, P.A.

[57] ABSTRACT

A retractable lead having a distal tip electrode is adapted for implantation on or about the heart and for connection to a system for monitoring or stimulating cardiac activity. The electrode includes a fixation helix for securing the electrode to cardiac tissue, which may or may not be electrically active. The electrode further includes an electrode tip having a mesh screen disposed on a surface at the distal end of the electrode tip, which can be used as a sensing or pacing interface with the cardiac tissue. The mesh screen provides a guiding mechanism for the helix as it travels out of the electrode for securing the electrode to the heart or other muscle or organ. The guiding mechanism may include a groove within the mesh screen. Alternatively, the guiding mechanism includes a guiding bar on which the fixation helix rides on during extension or retraction.

23 Claims, 6 Drawing Sheets

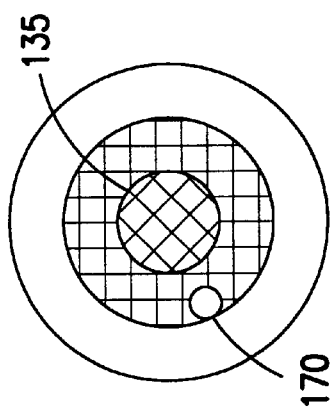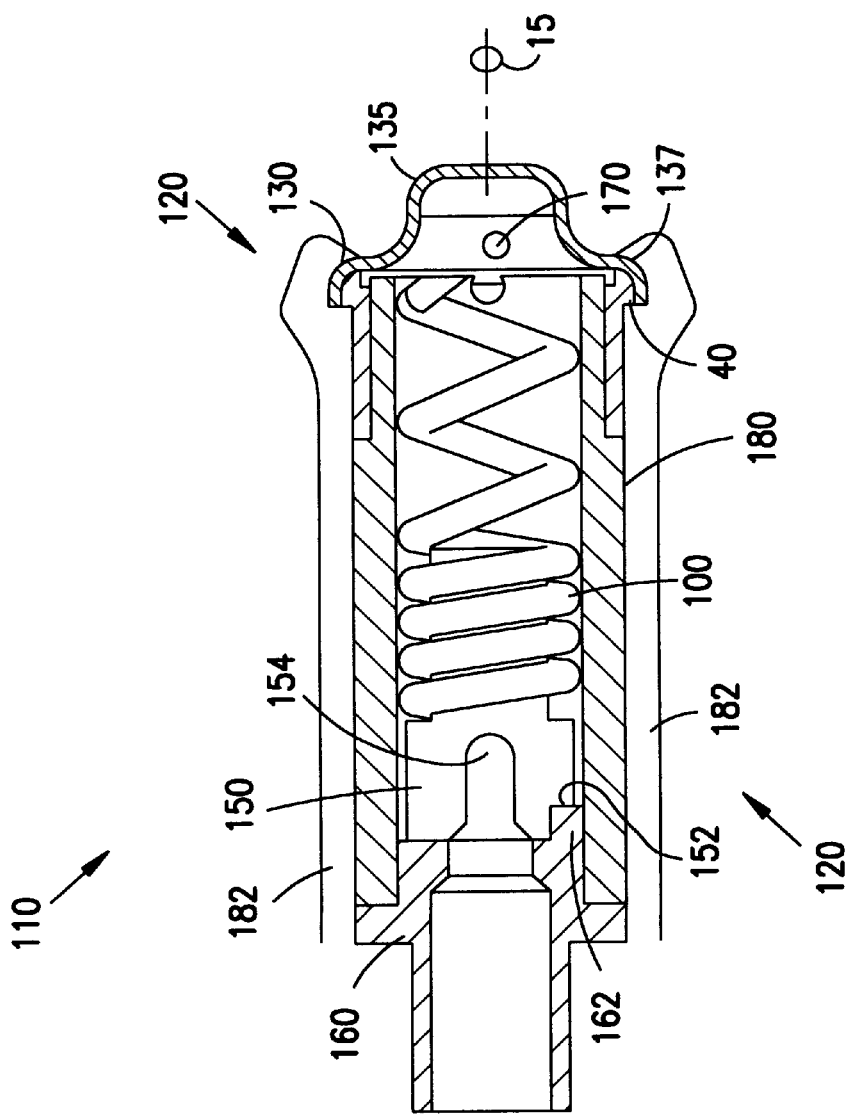

RETRACTABLE LEAD WITH MESH SCREEN

FIELD OF THE INVENTION

The present invention relates generally to leads for conducting electrical signals to and from the heart. More particularly, it pertains to an electrode tip for delivering electrical charges to the heart.

BACKGROUND OF THE INVENTION

Leads implanted in the body for electrical cardioversion or pacing of the heart are generally known in the art. In particular, leads implanted in or about the heart have been used to reverse (i.e., defibrillate or cardiovert) certain life threatening arrhythmias, or to stimulate contraction (pacing) of the heart. Electrical energy is applied to the heart via the leads to return the heart to normal rhythm. Leads have also been used to sense in the atrium or ventricle of the heart and to deliver pacing pulses to the atrium or ventricle. Tachy leads can sense, pace, and deliver defib shocks. Brady leads pace and sense the heart. Technically, the pacemaker or the automatic implantable cardioverter defibrillator (AICD) receives signals from the lead and interprets them. In response to these signals the pacemaker can pace or not pace. The AICD can pace, not pace or shock, and not shock. In response to the sensed bradycardia or tachycardia condition, a pulse generator produces pacing or defibrillation pulses to correct the condition. The same lead used to sense the condition is sometimes also used in the process of delivering a corrective pulse or signal from the pulse generator of the pacemaker.

Sick sinus syndrome and symptomatic AV block constitute the major reasons for insertion of cardiac pacemakers today. Cardiac pacing may be performed by the transvenous method or by leads implanted directly onto the ventricular epicardium. Most commonly, permanent transvenous pacing is performed using a lead positioned within one or more chambers of the heart. A lead, sometimes referred to as a catheter, may be positioned in the right ventricle or in the right atrium through a subclavian vein, and the lead terminal pins are attached to a pacemaker which is implanted subcutaneously. The lead may also be positioned in both chambers, depending on the lead, as when a lead passes through the atrium to the ventricle. Sense electrodes may be positioned within the atrium or the ventricle of the heart.

Pacemaker leads represent the electrical link between the pulse generator and the heart tissue which is to be excited. These pacemaker leads include single or multiconductor coils of insulated wire having an insulating sheath. The coils provide a cylindrical envelope, many times referred to as a lumen, which provides a space into which a stiffening stylet can be inserted. The conductive coil is connected to an electrode in an electrode assembly at a distal end of a pacing lead. Typically, a terminal member is mounted within a flexure sleeve at the proximal end of the pacing lead and connected to the proximal end of the conductive coil.

After the electrode assembly is positioned at a desired location within the heart, it is desirable to provide some method for securing the electrode assembly at that location. Mechanical fixation devices are used to firmly anchor the electrodes in the heart. One type of mechanical fixation device used is a corkscrew, or a helix. During placement of the lead, the tip of the lead travels intravenously through veins and the heart. While traveling through the veins, the helix at the tip of the lead may snag or attach to the side wall of the vein. Since this is highly undesirable as it may cause damage or other complications to a patient, retractable helixes have been provided for leads.

The helix is extended and screwed into the heart muscle by applying a torque to the other end of the conductor without use of any further auxiliary device or with a special fixation stylet. A lead must be capable of being firmly secured into the wall of the cardiac tissue to prevent dislodgement therefrom, while avoiding perforation of the electrode completely through the cardiac tissue.

There is a need for a body-implantable lead that has a helix for fixation to the wall of the atrium or ventricle of the heart. In addition, there is a need for a lead having an electrode for positioning within the atrium or ventricle that allows for tissue ingrowth. Tissue ingrowth further enhances the electrical performance of the lead. The lead and electrode are further stabilized within the heart as a result of tissue ingrowth.

SUMMARY OF THE INVENTION

According to the present invention, there is provided a body-implantable lead assembly comprising a lead, one end being adapted to be connected to electrical supply for providing or receiving electrical pulses. The lead further comprises a distal tip which is adapted to be connected to tissue of a living body. The lead also has a sheath of material inert to body materials and fluids and at least one conductor extending through the lead body.

The distal tip electrode is adapted for implantation proximate to the heart while connected with a system for monitoring or stimulating cardiac activity. The distal tip electrode includes an electrode tip, a mesh screen disposed at a distal end of the electrode tip, a fixation helix disposed within the electrode tip, and a helix guiding mechanism. The mesh screen is electrically active, but the area of the mesh screen can be changed to control electrical properties. Further, the mesh screen can entirely cover an end surface of the electrode tip, or a portion of the end surface in the form of an annular ring. In one embodiment, the helix guiding mechanism includes a hole punctured within the mesh screen. Alternatively, the helix guiding mechanism can include a guiding bar disposed transverse to a radial axis of the electrode. The helix is retractable, and is in contact with a movement mechanism. The movement mechanism provides for retracting the helix, such as during travel of the electrode tip through veins. The helix is aligned with the radial axis of the electrode and travels through the guiding mechanism.

In another embodiment, the electrode tip includes a mesh screen forming a protuberance on the end surface of the electrode tip. The protuberance is axially aligned with the radial axis of the electrode. The helix travels around the protuberance as it passes through the mesh while traveling to attach to tissue within the heart. The helix also travels around the protuberance as it is retracted away from the tissue within the heart. If the mesh screen is insulated around the protuberance, then a high impedance tip is created. Advantageously, the protuberance allows for better attachment to the cardiac tissue without having the electrode tip penetrating therethrough.

Additionally, a distal tip electrode is provided including an electrode tip, a mesh screen disposed at a distal end of the electrode tip, a fixation helix disposed within the electrode tip, and a helix guiding mechanism. The electrode tip further includes a piston for moving the helix. The piston further includes a slot for receiving a bladed or fixation stylet. When engaged and rotated, the piston provides movement to the helix. The base provides a mechanical stop for the helix and piston when retracted back in to the electrode tip.

In another embodiment, the distal tip assembly is adapted for implantation proximate to the heart while connected with a system for monitoring or stimulating cardiac activity. A fixation helix/piston assembly is housed by an electrode collar, housing, and base assembly. Attached to the proximal end of the helix is a piston which includes a proximal slot for receiving a bladed or fixation stylet. When a stylet is engaged in the slot and rotated, the piston provides movement to the helix. Depending on the embodiment, the fixation helix/piston assembly may be electrically active or inactive. The electrode collar, housing, and base all house the fixation helix/piston assembly. The proximal end of the electrode collar is attached to the distal end of the housing. Furthermore, the proximal end of the housing is attached to the distal end of the base, and the proximal end of the base is directly attached to the conductor coils of the lead.

A mesh screen is attached to the distal tip of the electrode collar. The mesh screen, in another embodiment, is electrically active and serves as the electrode on the distal tip assembly. The area of the mesh screen can be modified to cover differing portions of the end surface of the distal tip assembly to control electrical properties of the lead. The fixation helix travels through a guiding mechanism, where the guiding mechanism allows the fixation helix to be extended and retracted. In one embodiment, the helix guiding mechanism includes a hole formed within the mesh screen. Alternatively, the helix guiding mechanism can include a guiding bar disposed transverse to a radial axis of the electrode collar. The mesh screen and/or guiding bar also serve as a full extension stop when the helix is fully extended. The base serves as a stop when the fixation helix/piston assembly is fully retracted.

The provided electrode tip supplies a retractable helix and a mesh screen which advantageously allows for sufficient tissue in-growth. The guide mechanism provides a convenient way to direct the rotation of the helix. A further advantage of the electrode tip is the provided mechanical stop. The mechanical stop aids in preventing over-retraction of the helix during the installation or removal of the electrode tip.

| Brief Description of the Drawings |
| --- |
|
FIG. 3A is a cross-sectional view of an electrode tip of a lead for monitoring and stimulating the heart constructed in accordance with one embodiment of the present invention. |
|
FIG. 3B is an end view of the electrode tip of the lead shown in FIG. 3A. |
|

| -continued |
| --- |
| Brief Description of the Drawings |
|

BRIEF DESCRIPTION OF THE DRAWINGS

Figure 1:
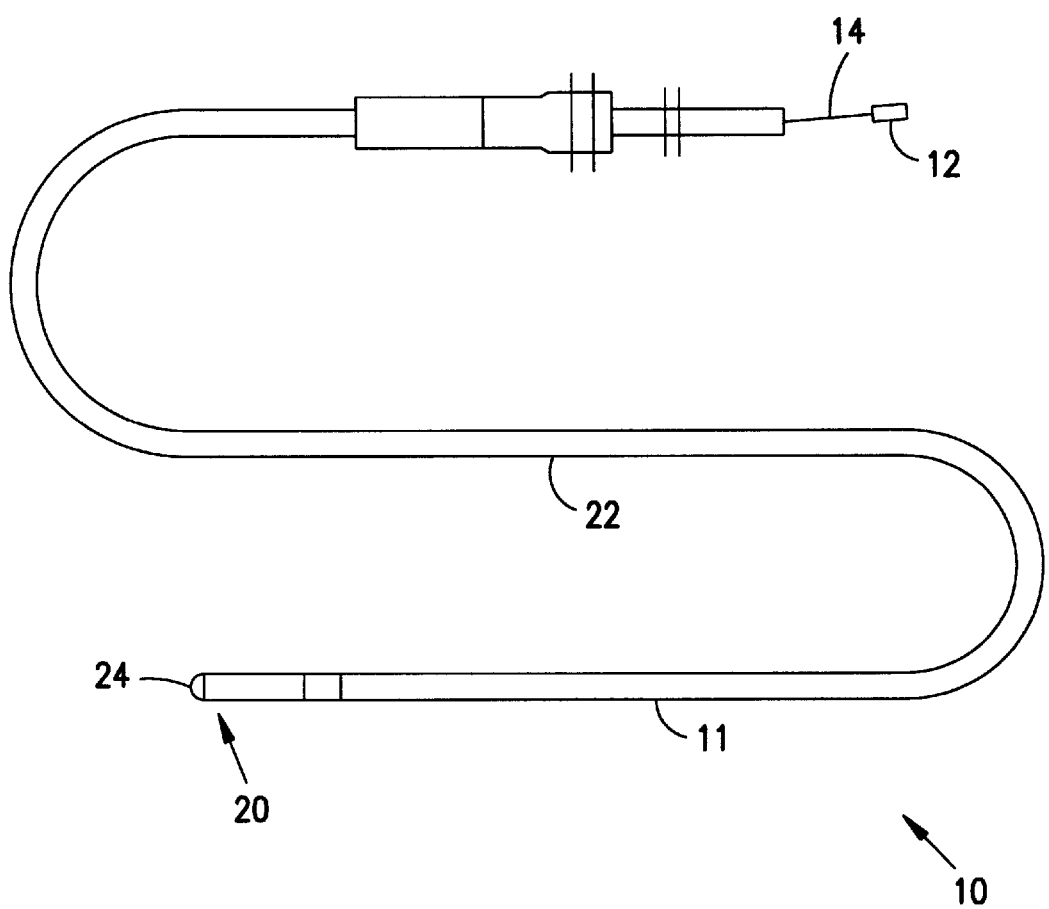
FIG. 1 is a first side elevational view illustrating a lead constructed in accordance with one embodiment of the present invention. |
|

FIG. 1 is a first side elevational view illustrating a lead constructed in accordance with one embodiment of the present invention.

Figure 2B:
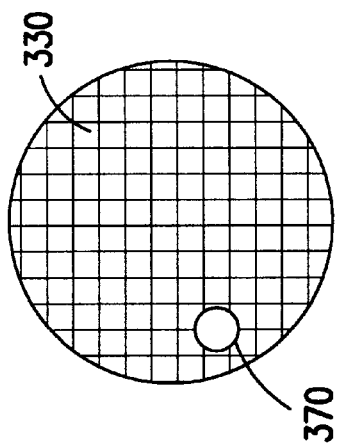
FIG. 2B is an end view of the electrode tip of the lead shown in FIG. 2A. |
|
Figure 2A:
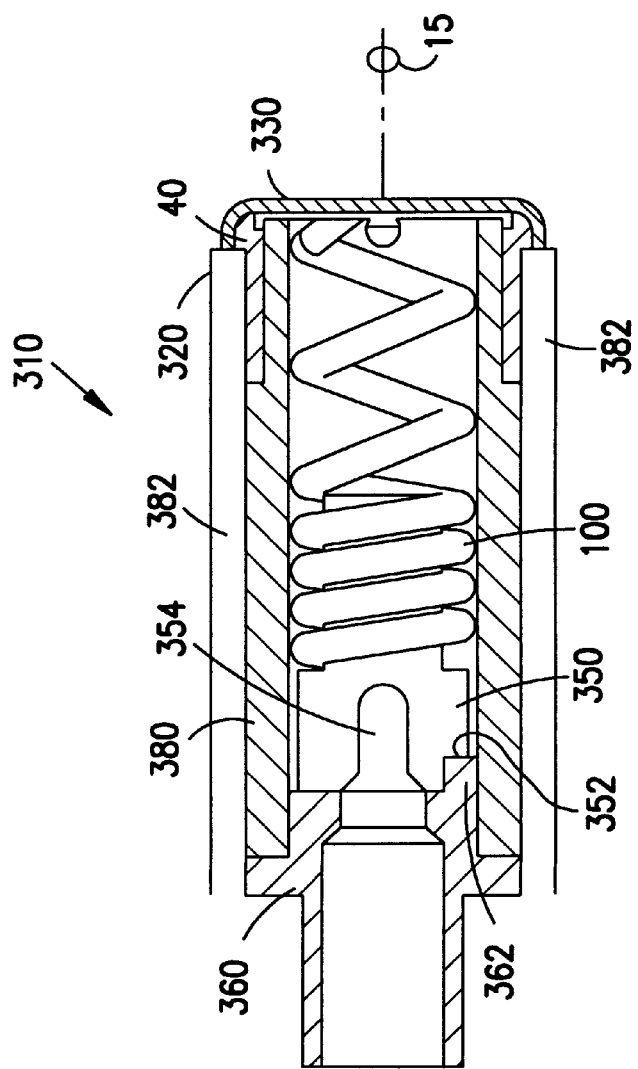
FIG. 2A is a cross-sectional view of an electrode tip of a lead for monitoring and stimulating the heart constructed in accordance with one embodiment of the present invention. |
|

FIG. 2A is a cross-sectional view of an electrode tip of a lead for monitoring and stimulating the heart constructed in accordance with one embodiment of the present invention.

FIG. 2B is an end view of the electrode tip of the lead shown in FIG. 2A.

FIG. 3A is a cross-sectional view of an electrode tip of a lead for monitoring and stimulating the heart constructed in accordance with one embodiment of the present invention.

FIG. 3B is an end view of the electrode tip of the lead shown in FIG. 3A.

Figure 4B:
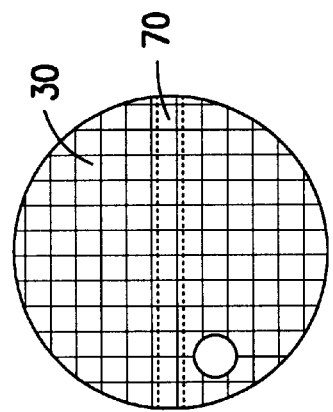
FIG. 4B is an end view of the electrode tip of the lead shown in FIG. 4A. |
|
Figure 4A:
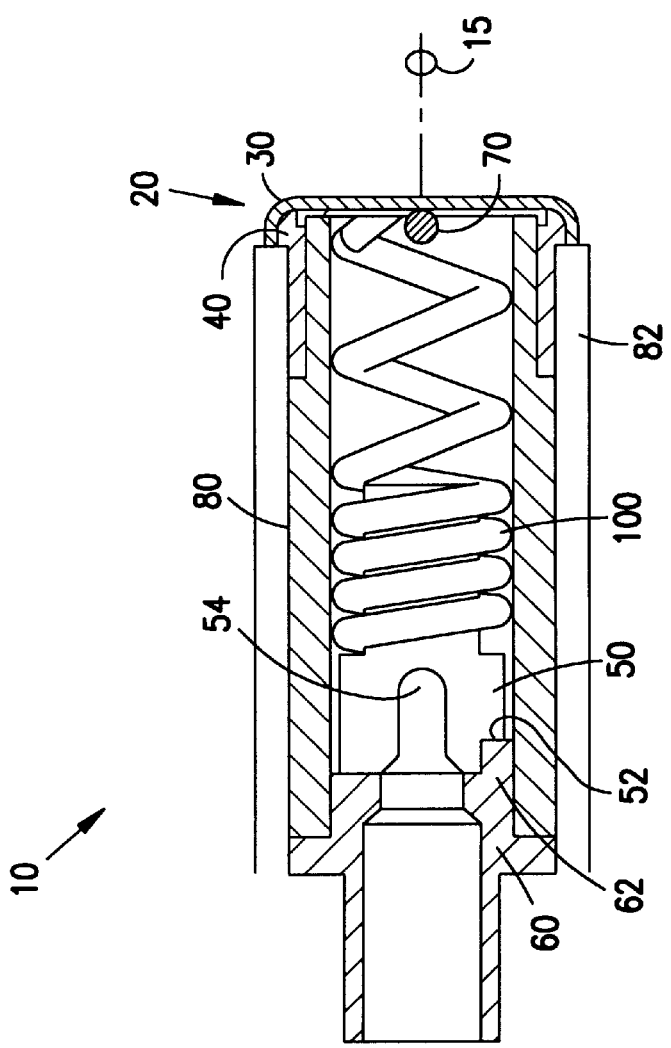
FIG. 4A is a cross-sectional view of an electrode tip of a lead for monitoring and stimulating the heart constructed in accordance with one embodiment of the present invention |
|

FIG. 4A is a cross-sectional view of an electrode tip of a lead for monitoring and stimulating the heart constructed in accordance with one embodiment of the present invention FIG. 4B is an end view of the electrode tip of the lead shown in FIG. 4A.

Figure 5B:
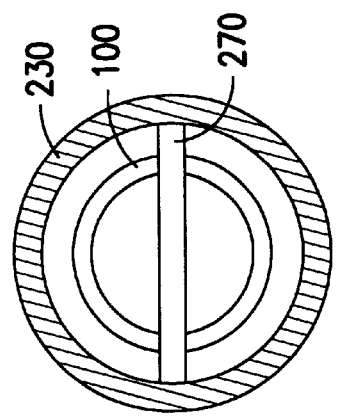
FIG. 5B is an end view of the electrode tip of the lead shown in FIG. 5A. |
Figure 5A:
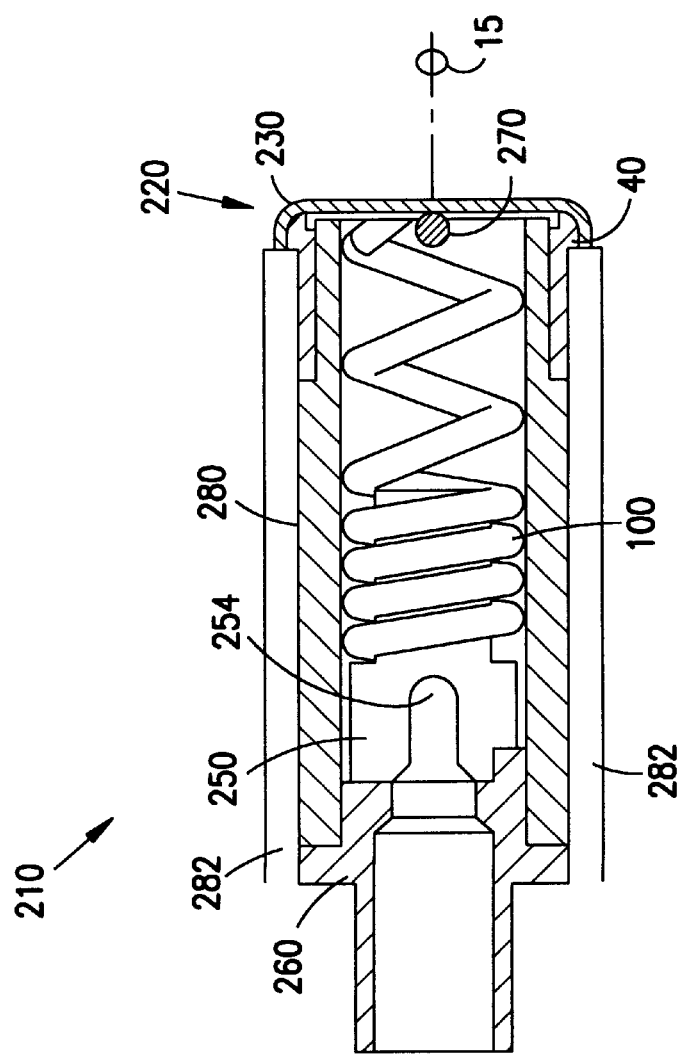
FIG. 5A is a cross-sectional view of an electrode tip of a lead for monitoring and stimulating the heart constructed in accordance with one embodiment of the present invention |
|

FIG. 5A is a cross-sectional view of an electrode tip of a lead for monitoring and stimulating the heart constructed in accordance with one embodiment of the present invention FIG. 5B is an end view of the electrode tip of the lead shown in FIG. 5A.

Figure 6:
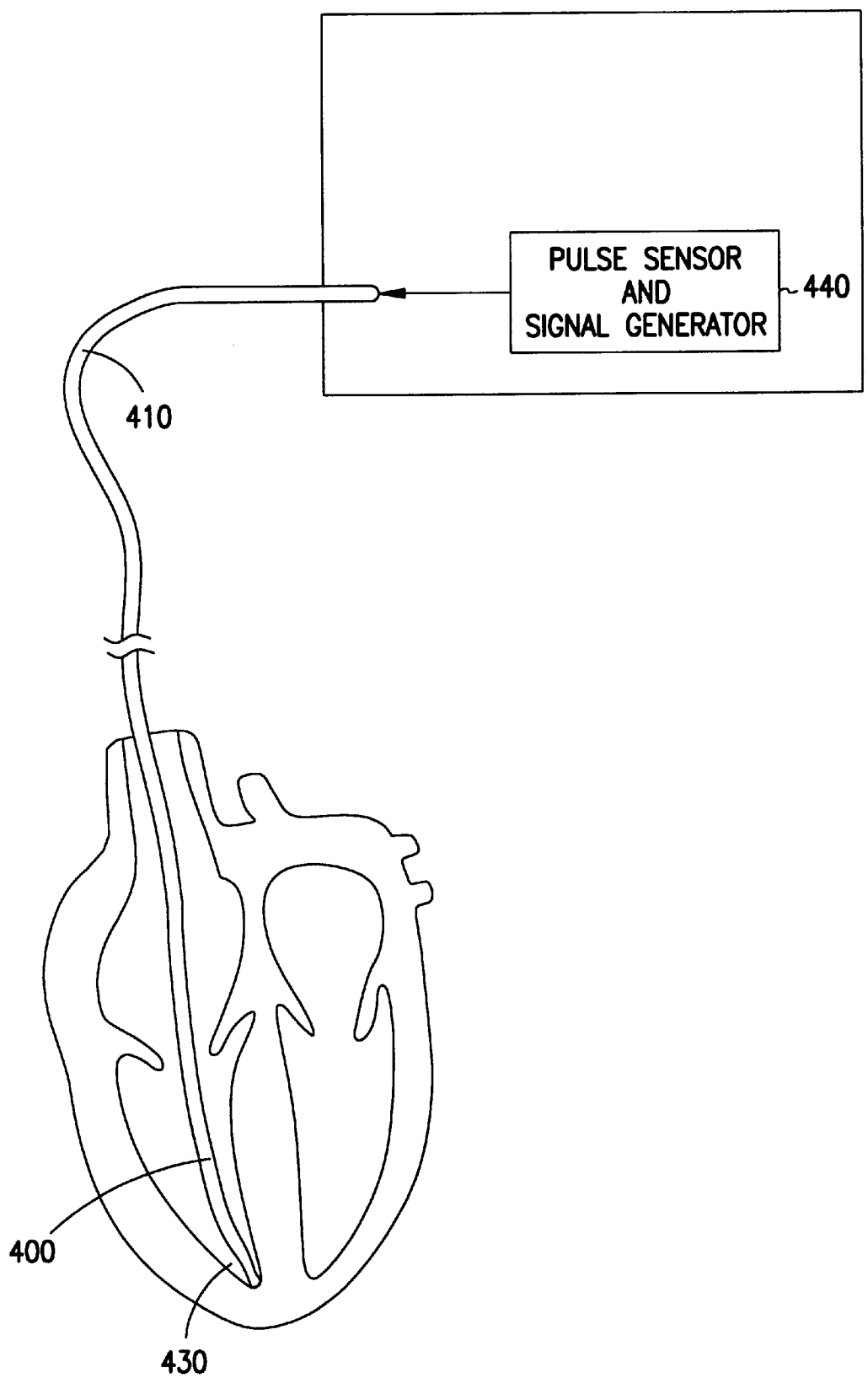
FIG. 6 is a cross-sectional view illustrating a system for delivering signals to the heart constructed in accordance with one embodiment of the present invention. |

FIG. 6 is a cross-sectional view illustrating a system for delivering signals to the heart constructed in accordance with one embodiment of the present invention.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims.

A lead 10 is illustrated in FIG. 1. The lead 10 comprises a lead body 11, an elongate conductor contained within the lead body, and a lead tip 20 with a retractable tip assembly 24 contained in the lead tip. In addition, a stylet 14 is shown inserted into the lead body 11. A helix 100 (FIGS. 2A–5A), which consists of an electrical conductor coil, is contained in the retractable lead tip. The helix 100 extends and retracts by rotation of the stylet 14, as will be discussed further below. A brady lead body is shown, although the invention could be incorporated with other leads, such as tachy leads. The lead body 11 consists of electrical conductors which are covered by a biocompatible insulating material 22. Silicone rubber or other insulating material can be used for covering the lead body 11.

In one embodiment, the helix 100 is formed of electrically conductive material offering low electrical resistance and also resistant to corrosion by body fluids. A platinum-iridium alloy is an example of a suitable material. Alternatively, the helix 100 is electrically inactive. In one embodiment, the helix 100 may be coated with an insulative material. A housing, described in further detail below, is made from an electrically conductive material and covered with a silicone rubber. The housing is directly connected to an electrical conductor within the lead 10. These materials are additionally suitable because they are inert and well tolerated by body tissue.

The helix defines a lumen and thereby is adapted to receive a stiffening stylet 14 that extends through the length of the lead. The stylet 14 stiffens the lead, and can be manipulated to introduce an appropriate curvature to the lead, facilitating the insertion of the lead into and through a vein and through an intracardiac valve to advance the distal end of the lead into the right ventricle of the heart. A stylet knob 12 is coupled with the stylet 14 for rotating the stylet 14 and advancing the helix into tissue of the heart.

In one embodiment, as shown in FIGS. 2A and 2B, a lead 310 has an electrode tip 320 which is provided with a mesh screen 330. The mesh screen 330 completely encapsulates the diameter of the lead, and serves as the pacing/sensing interface with cardiac tissue. If the helix is electrically active, it too can help serve as a pacing or sensing interface. The mesh screen 330 is of a porous construction, made of electrically conductive, corrosion resistant material. Using a mesh screen 330 having a porous construction allows for fibrotic ingrowth. This provides for a further anchoring of the lead tip 320 and also increases the sensing capability of the lead 310 by increasing the surface area in contact with the cardial tissue. The mesh screen 330 is attached to an electrode collar 40, which is electrically active. A housing 380, which is electrically conductive, encapsulates the piston 350 and the fixation helix 100. Insulation 382 is disposed about the housing 380 and collar 40.

Disposed within the lead 310 is a lead fastener for securing the lead 310 to cardiac tissue. The lead fastener can be disposed along the radial axis 15 of the electrode lead 310. In this embodiment, the lead fastener comprises a fixation helix 100. The fixation helix 100 can be made electrically active or inactive as discussed above. Attached to the fixation helix 100 is a piston 350. The piston 350 is configured to mate with a bladed locking stylet 14 at a stylet slot 354, and acts as an interface between the stylet 14 and the helix 100. The stylet 14, coupled the piston 350 at the stylet slot 354, extends and retracts the fixation helix 100 when the stylet 14 is rotated. The piston 350 can either be electrically active or inactive. The piston 350 also has a slot 352, which allows the piston 350 to mate with a base 360.

Fitted with a knob 362, as shown in FIG. 2A, the base 360 mates with the slot 352 of the piston 350. The base 360 serves as a stop once the fixation helix 100 is fully retracted. The electrically conductive base 360 also allows passage of a bladed locking stylet 14 and attachment of electrode coils.

In addition, the lead 310 has a guide groove 370. The groove 370 is formed by puncturing a hole within the mesh screen, although the guide groove can be formed by other methods known by those skilled in the art. Having a circular cross-section, the groove 370 has a diameter greater than that of the conductor forming the helix 100. The groove 370 is disposed within the mesh screen 330, and directs the fixation helix 100 from its retracted position, as illustrated in FIG. 2A, to an extended position (not shown). The groove 370 also directs the fixation helix 100 from an extended position to the retraction position.

In a second embodiment, as shown in FIGS. 3A and 3B, a lead 110 has an electrode tip 120 which is provided with a mesh screen 130. The mesh screen 130 completely encapsulates the diameter of the lead tip, and serves as the pacing/sensing interface with cardiac tissue. The screen 130 is of a porous construction, made of electrically conductive, corrosion resistant material. Using a mesh screen 130 having a porous construction allows for fibrotic ingrowth. This provides for a further anchoring of the lead tip 120 and also increases the sensing capability of the lead 110. The sensing capability is enhanced because the mesh screen 130 has more surface area than corresponding solid material. The ingrowth of fibrotic tissue into the mesh screen 130 increase the sensing capability of the lead 110 by increasing the surface area in contact with the cardial tissue. Furthermore, the geometry of the mesh screen, particularly the protuberance, as will be discussed below, creates a high pacing impedance tip.

The mesh screen 130 forms a protuberance 135 from a flat edge portion 137 of the mesh screen 130 in a generally central portion of the electrode tip 120. The protuberance 135 is generally circular in cross-section, and has a diameter smaller than a diameter of the lead 110. In addition, the protuberance 135 is aligned with the radial axis 15 of the lead 110. Sintered to an electrode collar 40, a process known by those skilled in the art, the mesh screen 130 is attached to the electrode tip 120. The electrode collar 40 is electrically active.

Disposed within the electrode lead 110 is a lead fastener for securing the electrode lead 110 to cardiac tissue. The lead fastener can be disposed along the radial axis 15 of the electrode lead 110. In this embodiment, the lead fastener comprises a fixation helix 100. The fixation helix 100 can be made electrically active or inactive to change sensing and pacing characteristics, as discussed above. Attached to the fixation helix 100 is a piston 150. The piston 150 is configured to mate with a bladed locking stylet 14, thereby providing a movement assembly. The stylet 14 extends and retracts the fixation helix 100 when the stylet 14 is rotated. The piston 150 can either be electrically active or inactive. The piston 150 also has a slot 152. The slot 152 of the piston 150 allows the piston 150 to mate with a base 160 upon full retraction.

The base 160 is modified with a knob 162 to mate with the slot 152 of the piston 150. The knob 162 mates with the piston 150 to prevent over-retraction once the helix 100 has been fully retracted. The stylet 14 operates to advance the fixation helix 100. As the implanter rotates the stylet 14, the stylet 14 engages the piston 150 at the stylet slot 154 and rotates the piston 150, which moves the fixation helix 100 through a guide groove 170. The guide groove 170 is for ensuring that the fixation helix 100 is properly guided out of and into the end of the electrode. Once the fixation helix 100 is fully retracted, the base 160 serves as a mechanical stop. The base 160 also allows passage of a bladed locking stylet 14 and attachment of electrode coils. Additionally, the base 60 is electrically active.

The electrode lead 110 also has a guide groove 170. The groove 170 is formed by puncturing a hole within the mesh screen. Having a circular cross-section, the groove 170 has a diameter greater than that of the conductor forming the helix 100. The groove 170 is disposed within the mesh screen 130, and directs the fixation helix 100 from its retracted position, as illustrated in FIG. 2A, to an extended position (not shown). During implantation, after the electrode is in contact with tissue at the desired location in the heart, the stylet 14 is rotated which causes the piston to advance the fixation helix out of the groove 170. As the fixation helix 100 is placed in an extended position, the helix 100 travels through groove 170 and circles around the protuberance 135. The groove 170 also directs the fixation helix 100 from an extended position to the retracted position. Advantageously, the mesh screen 130 prevents the implanter from overextension and advancing the helix 100 too far into the tissue. An electrically conductive housing 180 encapsulates both the piston 50 and the fixation helix 100. Insulation 182 covers the housing 180, the collar 40, and a portion of the mesh screen 130. The insulation 182 over the mesh screen 130 controls the impedance of the electrode tip 120.

In a third embodiment as shown in FIGS. 4A and 4B, a lead 10 has an electrode tip 20 which is provided with a mesh screen 30. The mesh screen 30 completely encapsulates the diameter of the lead tip. Sintered to an electrode collar 40, the mesh screen 30 is attached to the electrode tip 20. The electrode collar 40 is electrically active. A housing 80 is disposed about the helix 100, and is electrically active. Insulation 82, encompasses the housing 80 and collar 40.

Disposed within the lead 10 is a lead fastener for securing the lead 10 to cardiac tissue. The lead fastener can be disposed along the radial axis 15 of the lead 10. In this embodiment, the lead fastener comprises a fixation helix 100. The fixation helix 100 can be made electrically active or inactive to change sensing and pacing characteristics.

The helix 100 is of a well known construction. Using a conductor coil such as helix 100 has been shown to be capable of withstanding constant, rapidly repeated flexing over a period of time which can be measured in years. The helix 100 is wound relatively tightly, with a slight space between adjacent turns. This closely coiled construction provides a maximum number of conductor turns per unit length, thereby providing optimum strain distribution. The spirally coiled spring construction of helix 100 also permits a substantial degree of elongation, within the elastic limits of the material, as well as distribution along the conductor of flexing stresses which otherwise might be concentrated at a particular point.

Attached to the fixation helix 100 is a piston 50. The piston 50 is configured to mate with a bladed locking stylet 14. The piston 50 advances the fixation helix 100 once the lead is placed in position within the heart. The piston 50 can either be electrically active or inactive. The piston 50 also has a slot 52 and a stylet slot 54. The stylet 14 couples with the stylet slot 54 and extends or retracts the fixation helix 100 when the stylet 14 is rotated. The slot 52 of the piston 50 allows the piston 50 to mate with a base 60 when the helix 100 is retracted to prevent over retraction. The base 60 is configured with a knob 62 to mate with the slot 52 of the piston 50. Once the fixation helix 100 is fully retracted, the base 60 serves as a stop at full retraction. The base 60 also allows passage of a bladed locking stylet 14 and attachment of electrode coils. In addition, the base 60 is electrically active.

The lead 10 also includes a guiding bar 70. Extending across the diameter of the tip, the guiding bar 70 is generally cylindrical in shape. The guiding bar 70 directs the fixation helix 100 from its retracted position, as illustrated in FIG. 2A, to an extended position (not shown) as the piston 52 advances the helix 100. The guiding bar 70 also directs the fixation helix 100 as it is retracted from an extended position to the retraction position through the mesh screen. Although a guiding bar 70 is described, other types of guiding mechanisms can be used such as helical passageways, threaded housings, springs, and are considered within the scope of the invention. Additionally, the lead 10 is provided with a seal (not shown) for preventing entry of body fluids and tissue from entering the lead through the opening therein. The seal could be a puncture seal between the piston 50 and the base 60. Alternatively, O-rings could be used to seal the electrode.

In a fourth embodiment as shown in FIGS. 5A and 5B, a lead 210 has an electrode tip 220 which is provided with a mesh screen 230. The mesh screen 230 forms an annular ring having an open center, where the annular ring is centered at a radial axis 15 of the electrode lead 210. The mesh screen 230 provides more surface area than a smooth tipped electrode which aids in sensing. The removal of the center portion of the mesh screen creates a high impedance pacing tip due to the nature of the surface geometry. Sintered to an electrode collar 40, the mesh screen 230 is attached to the electrode tip 220. The electrode collar 40 is electrically active.

Disposed within the lead 210 is a lead fastener for securing the lead 210 to cardiac tissue. The lead fastener can be disposed along the radial axis 15 of the electrode lead 210. In this embodiment, the lead fastener comprises a fixation helix 100. The fixation helix 100 can be made electrically active or inactive as discussed above. Attached to the fixation helix 100 is a piston 250. The piston 250 has a stylet slot 254 and is configured to mate with a bladed locking stylet 14. The stylet 14, coupled with the piston 250 at the stylet slot 254, extends and retracts the fixation helix 100 when the stylet 14 is rotated. The piston 250 can either be electrically active or inactive. The base 260 serves as a stop once the fixation helix 100 is fully retracted. The base 260 also allows passage of a bladed locking stylet 14 and attachment of electrode coils. The base 60 is electrically active.

Additionally, the electrode lead also has a guiding bar 270. The guiding bar 270 directs the fixation helix 100 from its retracted position, as illustrated in FIGS. 5A and 5B, to an extended position (not shown). The guiding bar 270 also directs the fixation helix 100 from an extended position to the retracted position. Although a guiding bar 270 has been described, other types of mechanisms could be used to extend the helix, and are considered within the scope of the invention. A housing 280 encapsulates the piston 250 and the fixation helix 100, and insulation 282 is disposed over the housing 280 and collar 40.

FIG. 6 illustrates another embodiment, showing a view of a lead 400 for delivering electrical pulses to stimulate the heart. The lead 400 has an electrode end 430 and a connector terminal 410. The connector terminal 410 electrically connects the various electrodes and conductors within the lead body to a pulse generator and signal sensor 440. The pulse sensor and generator 440 contains electronics to sense various electrical signals of the heart and also produce current pulses for delivery to the heart. The pulse sensor and generator 440 also contains electronics and software necessary to detect certain types of arrhythmias and to correct for them. The lead terminal connector 410 provides for the electrical connection between the lead 400 and the pulse generator 440.

It is to be understood that the above description is intended to be illustrative, and not restrictive. Although the use of the lead has been described for use in a cardiac pacing system, the lead could as well be applied to other types of body stimulating systems. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A distal tip electrode adapted for implantation on or about the heart and for connection to a system for monitoring or stimulating cardiac activity, said electrode comprising:
   an electrode tip;
   a mesh screen disposed at a distal end of the electrode tip;
   a helix disposed within said electrode, said helix comprises a conductor disposed in a helical shape, wherein said helix is adapted for travel along a radial axis of the electrode through said distal end; and
   a helix guiding mechanism disposed within the mesh screen at said distal end, the helix guiding mechanism for directing movement of the helix during travel.

2. A distal tip electrode as recited in claim 1, wherein said mesh screen comprises an electrical conducting surface.

3. The distal tip electrode as recited in claim 2, wherein said mesh screen is electrically active.

4. The distal tip electrode as recited in claim 1, wherein said helix is aligned with a radial axis of the electrode.

5. The distal tip electrode as recited in claim 1, wherein said helix is electrically active.

6. The distal tip electrode as recited in claim 1, wherein said helix is electrically inactive.

7. The distal tip electrode as recited in claim 6, wherein said helix is made electrically inactive by a resistive coating.

8. The distal tip electrode as recited in claim 6, wherein said helix is made electrically inactive by forming the helix from a highly resistant material.

9. The distal tip electrode as recited in claim 1, wherein said helix is seated within said electrode tip.

10. The distal tip electrode as recited in claim 1, wherein said helix guiding mechanism comprises the mesh screen having a groove disposed therein.

11. The distal tip electrode as recited in claim 10, wherein said groove comprises an aperture formed within said mesh screen.

12. The distal tip electrode as recited in claim 10, wherein said groove has a circular cross-section.

13. The distal tip electrode as recited in claim 12, wherein said groove has a larger diameter than the conductor.

14. The distal tip electrode as recited in claim 1, wherein said mesh screen is sintered to the distal tip of the electrode tip.

15. A distal tip electrode adapted for implantation on or about the heart and for connection to a system for monitoring or stimulating cardiac activity, said electrode comprising:
   an electrode tip;
   a mesh screen disposed at a distal end of the electrode tip;
   a surface at the distal end of the electrode tip,
   a fixation device disposed within said electrode, said fixation device adapted for travel along radial axis of the electrode through said surface; and
   a guiding mechanism disposed within the mesh screen at said surface, the guiding mechanism for directing movement of the fixation device during travel;
   a movement assembly, said movement assembly for providing movement to said fixation device.

16. The distal tip electrode as recited in claim 15, wherein said fixation device comprises a helix.

17. The distal tip electrode as recited in claim 15, wherein said movement assembly comprises a piston.

18. The distal tip electrode as recited in claim 17, wherein the piston has a slot disposed therein, and a base further comprises a knob, said slot for mating with said knob.

19. The distal tip electrode as recited in claim 18, wherein the slot mated with said knob are adapted to form a stop mechanism for said fixation device.

20. The distal tip electrode as recited in claim 17, wherein said distal tip electrode further comprises a seal, said seal disposed between said piston and a base.

21. The distal tip electrode as recited in claim 15, wherein the mesh screen has a groove guide disposed therein.

22. An electrode adapted for implantation on or about the heart and for connection to a system for monitoring or stimulating cardiac activity, said electrode comprising:
   a lead body having a first end and a second end;
   an electrode disposed proximate the first end of the lead body;
   connector terminal disposed at said second end of the lead body, said connector terminal for connecting with a pulse generating unit;
   an electrode tip disposed proximate one end of the electrode;
   a surface at the distal end of the electrode tip, said surface further comprising an electrical conducting surface wherein said surface is comprised of a mesh screen;
   a helix disposed within said electrode, said helix comprising a conductor disposed in a helical shape, wherein said helix travels along radial axis of the electrode through said surface thereby placing said helix in extension and retraction; and
   a helix guiding groove disposed within the mesh screen at said surface, the helix guiding groove for directing movement of the helix during extension and retraction of said helix.

23. A system for delivering signals to the heart, said system comprising:
   an electronics system including a cardiac activity sensor and a signal generator for producing signals to stimulate the heart; and
   a lead adapted for implantation heart, said lead comprising:
      an electrode tip;
      a mesh screen disposed at a distal end of the electrode tip;
      a surface at the distal end of the electrode tip,
      a helix disposed within said electrode, said helix comprises a conductor disposed in a helical shape, wherein said helix travels along radial axis of the electrode through said surface; and
      a helix guiding mechanism disposed within the mesh screen at said surface, the helix guiding mechanism for directing movement of the helix during travel.

* * * * *

UNITED STATES PATENT AND TRADEMARK OFFICE
CERTIFICATE OF CORRECTION

PATENT NO. : 6,097,986
DATED : August 1, 2000
INVENTOR(S) : Janke et al.

It is certified that error appears in the above-identified patent and that said Letters Patent is hereby corrected as shown below:

Claims,
Please renumber claims 14 through 23 as claims 18 through 27.
After claim 13, please insert the following claims:

-- 14. The distal tip electrode as recited in claim 1, wherein said helix guiding mechanism comprises a guiding bar.

15. The distal tip electrode as recited in claim 14, wherein said guiding bar comprises a cyliner disposed proximate to said surface.

16. The distal tip electrode as recited in claim 14, wherein said guiding bar is disposed transverse to said radial axis of said electrode.

17. The distal tip electrode as recited in claim 1, wherein said mesh screen comprises an annular ring, said annular ring having an open center. --

After renumbered claim 27, please insert the following claims:

-- 28. The distal tip electrode as recited in claim 1, further comprising a protuberance extending from said mesh screen.

29. The distal tip electrode as recited in claim 28, wherein the protuberance is formed of the mesh screen.

30. The distal tip electrode as recited in claim 28, wherein the protuberance is disposed along said radial axis.

31. The dital tip electrode as recited in claim 28, wherein said helix guiding mechanism comprises a groove disposed within said mesh screen.

UNITED STATES PATENT AND TRADEMARK OFFICE
CERTIFICATE OF CORRECTION

PATENT NO.   : 6,097,986
DATED        : August 1, 2000
INVENTOR(S)  : Janke et al.

It is certified that error appears in the above-identified patent and that said Letters Patent is hereby corrected as shown below:

32. The distal tip electrode as recited in claim 28, wherein said protuberance is positioned such that the helix coils around said protuberance as the helix is advanced along the radial axis.

33. The distal tip electrode as recited in claim 28, wherein said protuberance has a generally circular cross-section. --

Signed and Sealed this

Thirteenth Day of November, 2001

*Attest:*

*Attesting Officer*

NICHOLAS P. GODICI
*Acting Director of the United States Patent and Trademark Office*